United States Patent [19]

Nicolau et al.

[11] Patent Number: 4,938,947
[45] Date of Patent: Jul. 3, 1990

[54] AEROSOL COMPOSITION FOR IN VIVO IMAGING

[75] Inventors: Yves-Claude Nicolau, La Chapelle; Alain Le Pape, Langeais; Rita Barot-Ciorbaru, Fontenay-Aux-Roses, all of France

[73] Assignee: Centre National De La Recherche Scientifique (CNRS), France

[21] Appl. No.: 142,242

[22] Filed: Jan. 4, 1988

Related U.S. Application Data

[63] Continuation of Ser. No. 794,500, Nov. 1, 1985, abandoned.

[51] Int. Cl.$^5$ ............... A61K 49/02; A61K 49/00
[52] U.S. Cl. .................. 424/1.1; 424/7.1; 424/9; 424/92; 424/450
[58] Field of Search ............ 424/1.1, 9, 7.1, 92, 424/450

[56] References Cited

U.S. PATENT DOCUMENTS

| | | | |
|---|---|---|---|
| 4,042,678 | 8/1977 | Ciorbaru et al. | 424/12 |
| 4,201,768 | 5/1980 | Ciorbaru nee Sfartz et al. | 424/92 |
| 4,280,991 | 7/1981 | Burch | 424/1.1 |
| 4,396,607 | 10/1983 | Lefrancier et al. | 424/85 |
| 4,409,209 | 10/1983 | Baschang et al. | 514/8 |
| 4,544,545 | 10/1985 | Ryan et al. | 424/1.1 |
| 4,590,060 | 5/1986 | Ehrenfeld | 424/1.1 |

OTHER PUBLICATIONS

Dictionary of Microbiology, Wiley–Interscience Pub., p. 1055 (1979).
Dictionary of Scientific and Technical Terms, 3rd Ed., McGraw-Hill Book Co. (1984), p. 257.

*Primary Examiner*—Howard J. Locker
*Assistant Examiner*—J. E. Thomas
*Attorney, Agent, or Firm*—Handal & Morofsky

[57] ABSTRACT

The present invention relates to an aerosol composition for in vivo imaging or ex vivo diagnosis of tumors, which composition contains one or more soluble fragments of bacterial wall or cell peptidoglycan or equivalent synthetic compounds which are labelled with a radioactive, paramagnetic or fluorescent element and encapsulated in liposomes and a substrate which can be used for administration by aerosol.

8 Claims, 6 Drawing Sheets

AEROSOL COMPOSITION FOR IN VIVO IMAGING

This application is a continuation, of application Ser. No. 794,500, filed Nov. 1, 1985, now abandoned.

The present invention relates to compositions intended more especially for in vivo imaging, mainly by scintigraphy but also by other diagnostic techniques, such as nuclear magnetic resonance or fluorescence. The present invention is also applicable to the ex vivo diagnosis of tumors.

In vivo imaging techniques by scintigraphy are known, and consist in using a vector agent labelled with a radioactive element, which vector agent becomes bound specifically to cells which it is desired to visualize. This type of examination is used, in particular, for detecting and demonstrating pathological conditions involving tumors and those involving inflammation.

The compositions according to the present invention were shown to be especially effective in this type of application.

More especially, these compositions are aerosol compositions for in vivo imaging or ex vivo diagnosis of tumors, which compositions contain one or more soluble fragments of bacterial wall or cell peptidoglycan or equivalent synthetic compounds which are labelled with a radioactive, paramagnetic or fluorescent element and encapsulated in liposomes and a substrate which can be used for administration as an aerosol.

Soluble peptidoglycans and fractions containing soluble fragments of peptidoglycans originating from the bacterium or bacterial wall of Nocardiae have been described in French Patent Nos. 2,345,158, 2,268,531 and 2,345,159 (U.S. Pat. Nos. 4,042,678 and 4,201,768).

These are peptidoglycans extracted from the essentially delipidized and deproteinized walls or from the cells of three strains of Nocardia, *N. opace, N. corallina* and *N. rubra*, which are delipidized, treated with enzymes and subjected to various purification processes.

The fractions obtained have a multiplicity of potentialities in addition to their mitogenic activity (R. Ciorbaru et al., Infect. Immun. 1975, 11, 257). These fractions possess a range of other properties, such as antitumor activity (R. Barot-Ciorbaru et al., Int. J. Immunopharmacol. 1981, 3, 115), capacity to induce circulating interferon (R. Barot-Ciorbaru et al., Infect. Immun. 1978, 19, 353 and J. Reticuloendothel. Soc. 1981, 30, 247), to activate NK cells (R. Barot-Ciorbaru et al., J. European, Jerusalem Congress Sept. 8–13, 1985), and to inhibit the growth of pulmonary metastases (3LL) in $C_{57}Bl_6$ mice; in Wistar AG rats, treatment with these fractions reduces the frequency of ganglionic and pulmonary metastases in the case of a rat rhabdomyosarcoma (R. Barot-Ciorbaru et al., Forum de Cancerologie, Paris 10–11/VI, 1985). Macrophages are directly or indirectly involved in most of these activities; in effect, the addition of these fractions to mouse or rat resident peritoneal macrophages causes them to secrete, in addition, $Il_1$ and other monokines (R. Barot-Ciorbaru et al., C.R. Acad. Sc. Paris 1984 v. 298, series III, No. 17).

Furthermore, it is possible to replace these fragments by equivalent synthetic compounds, that is compounds obtained by synthesis or hemisynthesis, and including in their formula elements of structure contained in the said soluble fragments mentioned before. It could be especially a simplified synthetic structure the manipulation of which is easier.

*N. opaca* ATCC 21,953, synonymes *Mycobacterium opacum* or *Proactinomyces opacus*, cells (gram-positive, aerobic, nonpathogenic) are cultured in accordance with the conditions described in the abovementioned patent. The culture time of 48 h can be reduced to 24 h.

The bacterial cells obtained are separated from their culture medium by centrifugation. The moist cells are subsequently subjected to a treatment for extraction of the lipids which they contain, using one or more organic solvents.

The cells are initially suspended in 30 times their weight of acetone at room temperature for 48 hours on a magnetic stirrer. This procedure is repeated several times. The cells are then delipidized under reflux in a Soxhlet type extractor using pure solvents (acetone, alcohol, ether, chloroform or an 83:17 chloroform/methanol azeotropic mixture). The total extracted lipids reach 40% of the dry weight of the cells. The cells are then resuspended in acetone, decanted and dried.

The delipidized cells are suspended in 100 times their weight of water, and 0.2 mg of DNase per 100 ml of suspension is added to destroy the deoxyribonucleic acid. The suspension is centrifuged at 27,500 g and at 40° C. for one hour.

The cells are again suspended in 0.1M ammonium acetate at pH 6.2 in the presence of 0.1% of chicken egg white lysozyme, and then incubated for 10 hours at 37° C., a few drops of toluene being added to prevent contamination.

The suspension is centrifuged and the cells are incubated a second time under the same conditions. The two extracts are mixed, lyophilized and taken up with water to remove the ammonium acetate.

The two extracts obtained are then delipidized by three successive extractions at room temperature with ether, and then dried. 500 mg of Nocardia extract are placed on a Sephadex G-75 column equilibrated with 0.1M acetic acid, and eluted with the same solution. The fraction known as NSPD (NSPD: nocardia soluble peptidoglycan derivative) consists of 18–20 4-ml tubes, the content of which is opalescent, and the tube contents are reunited and lyophilized. The NSPD fraction represents 50% of the pool of the starting material.

NSPD is a white powder which has a flocculent appearance. It is soluble in water alkalinized with 0.1M NaOH pH 10.5 or in 0.03M sodium citrate, 0.5M NaCl at pH 9.4.

The elementary chemical analysis shows the following values:

| | CONTENTS EXPRESSED AS GRAMS PER 100 g OF PRODUCTS | | | | |
|---|---|---|---|---|---|
| | C | H | N | S | P |
| NSPD | 14.57 | 5.82 | 11.64 | 0.16 | 3.05 |

NSPD is heterogeneous. It contains:

| | |
|---|---|
| neutral sugars | 25–30%. |
| amino sugars | 19–25%, |
| amino acids | 32–35%, |
| DAP (diaminopimelic acid) | 200 nmol/mg, |
| lipids | 7%. |

Its heterogeneity could be further demonstrated by means of several techniques:

by sedimentation at a speed of 59,780 rpm at 20° C. in phosphate buffer $\mu=0.1$, pH 11.8 at a concentration of 5 mg/ml. A peak is obtained which is not clearly separated and represents a heterogeneous mixture of the products (Beckman ultracentrifuge);

by treatment with Folch's mixture (chloroform/methanol/water, 16:8:6 v/v), after 16 hours 3 phases are obtained: 50% aqueous, 30% organic and 20% interphase;

by molecular sieve HPLC chromatography on a TSK 2000 column, 4 fractions are obtained.

The NSPD according to the present invention is hence characterized by its heterogeneity since, depending on whether it is treated with Folch's mixture or whether it is subjected to HPLC, 3 phases or 4 distinct fractions, respectively, are obtained.

Furthermore, after separation by HPLC, the NSPD activity can be found in one or more fractions.

It is of course possible, as described in the patents already mentioned, to use peptidoglycans originating from walls of other bacteria, but in the context of the present invention it will be preferable to use in particular the abovementioned derivative referred to as "NSPD" which originates from a strain of Nocardia.

The NSPD is labelled with a compound and, for reasons of convenience, this compound will, for the most part, be radioactive. $^{99m}$Tc (technetium), the technique for labelling of which is reliable and rapid, and the half-life of which enables scintigraphic examinations to be carried out on man, will preferably be used.

As regards the liposomes employed, these can be multilamellar liposomes (MLV) or unilamellar liposomes (ULV), more especially consisting of phospholipids, such as phosphatidylcholine and phosphatidylserine, and cholesterol, especially in the mole ratio 4:1:5.

These liposomes can be produced according to known techniques, for example by the process of Bangham by hydration of lipids (J. Mol. Biol. 1965, 13, 238–252), by reverse phase evaporation (REV) according to Szoka and Papahadjopoulos (Proc. Nat. Acad. Sci. U.S.A., 1978, 75, 4194–4198) or by sonication of a dispersion of phospholipids (Biochemistry, 1977, 16, 2806–2810), and the like.

The trials performed showed that identical results were obtained from liposomes the size of which was between 50 nm and 500 nm and which had to consist of at least one phospholipid compound possessing surface-tant properties.

Encapsulation of the NSPD can be performed by adding it to the aqueous phase during the formation of the liposomes, or possibly by incubation with the liposomes for 30 minutes at 20° C. with intermittent stirring, taking into account the amphiphilic nature of NSPD.

The essential characteristic of the compositions according to the present invention is that they are used for administration by aerosol.

The trails performed showed, in effect, that no administration route other than by aerosol led to any satisfactory result.

Naturally, the formation of the aerosol from the composition of liposomes and NSPD may be produced by known techniques, employing suitable systems which will have to deliver particles of diameter less than 10 micrometers, most commonly using air as a carrier gas.

It is, however, recommended, when carrying out and implementing the inhalation process, to take care to avoid external contamination of the patients by the radio-active product in aerosol form, in order to avoid falsely positive scintigraphic results. It is also recommended to install a suitable aspiration device designed to prevent contamination of the air in the premises by the radio-active product in aerosol form during administration to the patients.

The compositions according to the present invention can be made more specific by fractionating the NSPD extracts or by making use of other wall peptidoglycans. For each of these, it will naturally be appropriate to determine their specificity.

Other advantages and characteristics of the invention will emerge on reading the examples and figures which follow.

FIGS. 1A, 1B and 1C show the scintigrams of a patient No. 1 bearing a malignant melanoma of the right orbit and a metastasis on the dome of the skull.

FIGS. 2A, 2B and 2C show the results of scintigraphy after inhalation of liposomes containing 30 mCi of $^{99m}$Tc-NSPD (A and B) and monitoring of the ventilation with xenon 133 (C) in a patient No. 2 bearing a non-keratinizing epithelial carcinoma of the right lung (thorax posterior face).

FIGS. 3A, 3B and 3C show the scintigrams obtained 1 hour after inhalation of liposomes containing 30 mCi of $^{99m}$Tc-NSPD in a patient No. 3 suffering from infiltration of the thigh, the leg and the foot after ablation of a melanosarcoma of the sole of the right foot and a metastatic ganglion of the right groin. The views A, B and C correspond, respectively, to the thighs, knees and legs.

FIG. 4 shows the anterior face scintigram obtained 1 h 30 min after inhalation of liposomes containing 30 mCi of $^{99m}$Tc-NSPD in a patient No. 4 suffering from a metastatic ganglion of the right groin and a chain of subcutaneous metastases of a melanosarcoma.

FIGS. 5A and 5B show the scintigrams obtained 1 h (A) and 6 h (B) after inhalation of $^{99m}$Tc-NSPD encapsulated in liposomes by a patient No. 5 suffering from pulmonary metastases of a small cell carcinoma of the base of the tongue (thorax anterior face).

FIG. 6 shows the size distribution of the liposomes in the preparation of Example 1.

EXAMPLE 1

The scintigraphic examinations described below were carried out with NSPD preparations which were shown to be active for the detection of pulmonary carcinomas and metastases after obtaining the consent of the patients and the agreement of the Commission d'Ethique [Ethical Commission] of the Centre Hospitalier Universitaire of Tours (France).

After monitoring the sterility and absence of pyrogens (in vivo test in rabbits and "limulus test," Mallinckrodt, Inc., in vitro), the preparations dissolved in isotonic saline solution are labelled with the $^{99m}$Tc-Sn complex according to the following procedure derived from the technique of Osborne et al. (Int. J. Nucl. Med. Biol., 1982, 9, 47–51): 400 $\mu$g of lyophilized NSPD dissolved in 400 $\mu$l of 0.15M NaCl are reduced under vacuum with 600 $\mu$g of anhydrous stannous chloride for 15 minutes, and then complexed with 40 to 80 mCi of 99m-(sodium pertechnetate) eluted as the time of use with 0.15M NaCl solution from a generator (C.E.A., France).

The labelling yield of the NSPD preparation assessed by partition chromatography in methanol/water (70:30 v/v) solvent should be 99.5% at least.

This labelled preparation is then encapsulated in liposomes of phosphatidylcholine, phosphatidylserine and cholesterol, for example in the mole ratio 4:1:5.

The technique employed for preparing the liposomes is as follows: the phospholipids and cholesterol are mixed in chloroform. After evaporation of the solvent, the lipids are deposited as a film on the wall of the vessel, and the residual solvent is removed in 30 to 45 minutes under a stream of nitrogen. To the lipid film, PBS buffer at pH 7.4 is added, so as to obtain a final phospholipid concentration of 1 mg/ml in the aqueous phase. After sonication for 25 minutes at +2° C. under nitrogen, monitoring of the size of the liposomes is performed by electronic microscopy.

After incubation under vacuum of 5 ml of liposomes and the labelled NSPD solution for 30 minutes at room temperature, the final preparation is sterile, pyrogen-free, of pH between 7.2 and 7.5 and contains less than 1% of free $^{99m}$Tc.

The size distribution of the liposomes in this preparation is illustrated in FIG. 6.

This is the preparation which is administered to the patients using a TV 6000 Siemens ultrasonic microinhaler (Germany) in an E.S.I. air filtration hood (France).

EXAMPLE 2

The scintigraphic examinations are carried out from 1 h to 24 h after inhalation of the aerosol, with a Nuclear Chicago gamma camera equipped with a high resolution 140 keV parallel collimator, the data being processed on a SIMIS III computer (SOPHA MEDICAL - FRANCE).

The thyroid of the patients is protected from the binding of technetium possibly dissociated in vivo by administration of 400 mg of $NaClO_4$ per os 30 minutes before the beginning of the test.

To reduce the secretion of saliva and avoid premature contamination of the esophagus and digestive system, the patients also receive 0.25 to 0.50 mg of atropine sulfate subcutaneously 45 minutes before the inhalation.

The examinations were performed initially on patients who had not received chemotherapy or radiotherapy for 1 month in order to avoid falsely negative results, but the final trials carried out led to generally satisfactory results with patients subjected to these therapies.

Patient 1

Figure 1A:
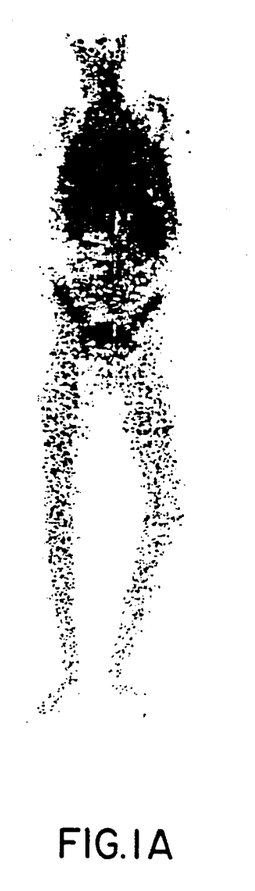
Figure 1B:
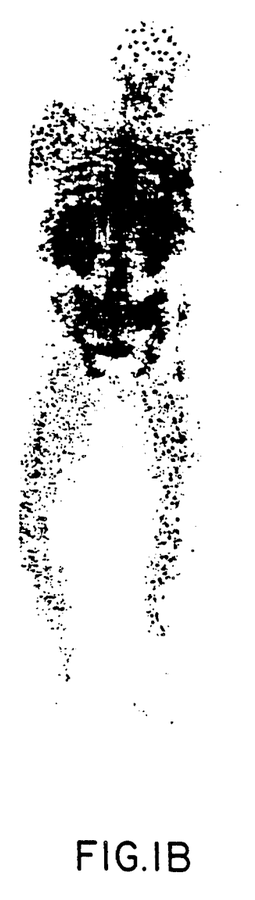
Figure 1C:
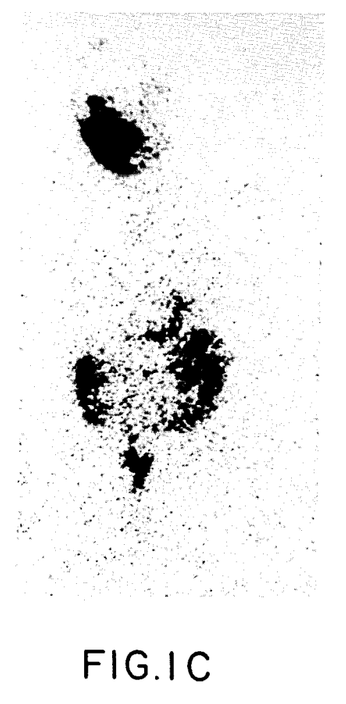

The results of the imaging of patient 1 are shown in FIGS. 1A, 1B and 1C.

These figures show the whole body scintigram of a patient bearing a malignant melanoma of the right orbit and a metastasis on the dome of the skull.

FIGS. 1A and 1B were produced after intravenous injection of $^{99m}$Tc-labelled NSPD, and the tumor components are not absolutely clearly demonstrated by this mode of administration (FIG. 1A=posterior face; FIG. 1B=anterior face).

FIG. 1C was produced after inhalation of $^{99m}$Tc-NSPD encapsulated in liposomes according to the procedure described in Example 1 (anterior face). The demonstration of the two tumors mentioned is noted.

It is appropriate, furthermore, to comment that, while in the photo the non-specific binding is predominant, with a visualization of the whole of the body, the liver and the spleen, in contrast, in the case of the scintigram labeled 1C, only certain components, and especially the tumor components are visualized. The background is very weak in FIG. 1C.

Patient 2

This patient has a non-keratinizing epithelial carcinoma of the right lung.

Figure 2A:
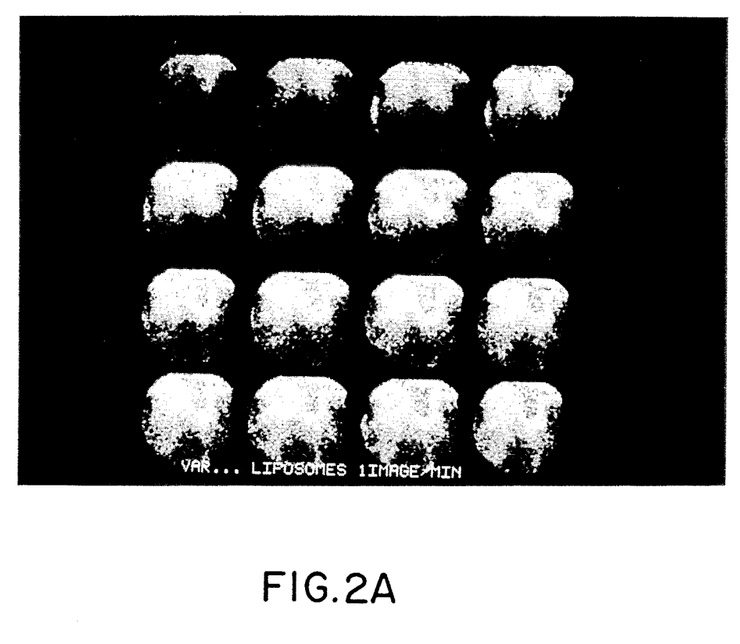

FIG. 2 shows in A the different exposures of a dynamic scintigram (60 sec/image) obtained from 0 to 16 minutes during inhalation of the liposomes according to the present invention.

Figure 2B:
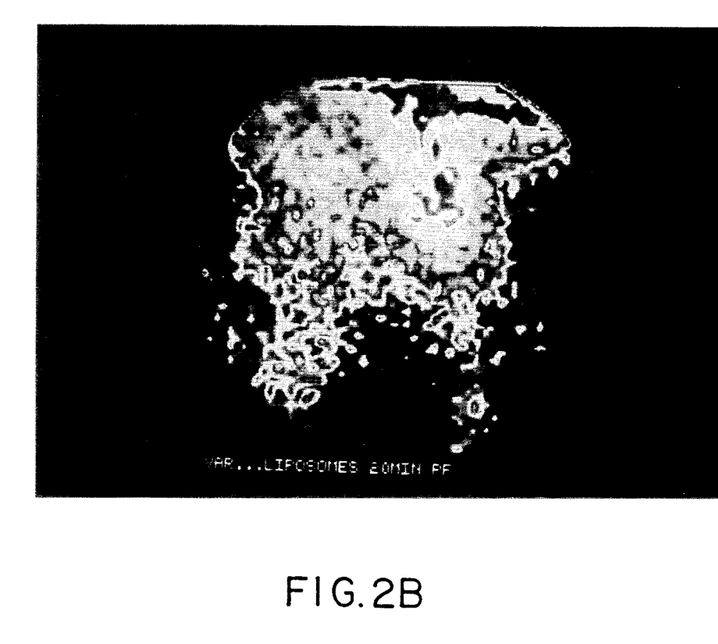

FIG. 2B, obtained 20 minutes after the beginning of the inhalation (static scintigraphy) shows objectively the hyper-binding of the tracer at the level of the right lung where the tumor is sited and the quantification of the radioactivity at the level of the region of interest and of the contralateral healthy zone.

Figure 2C:
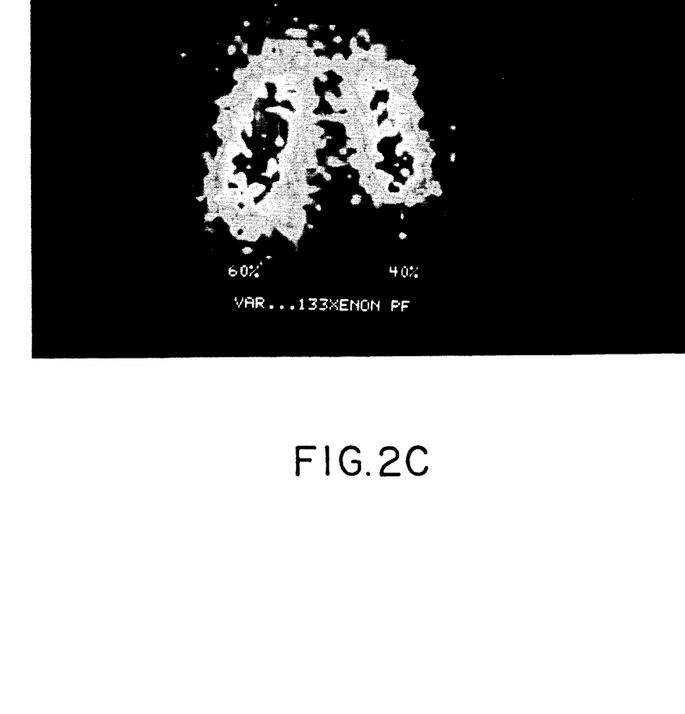

FIG. 2C corresponds to the monitoring of the ventilation by xenon-133 scintigraphy. This examination shows objectively a hypoventilation of the tumor-bearing right lung in which 40% of the radioactivity is sited whereas the healthy left lung has an activity of 60%. This examination shows that the focus of early binding obtained with the $^{99m}$Tc-Sn-NSPD-liposome preparation and shown in FIGS. A and B genuinely results from an accumulation of the tracer in the tumor-bearing lung and does not correspond to an effect due to ventilation.

Patient 3

Figure 3A:
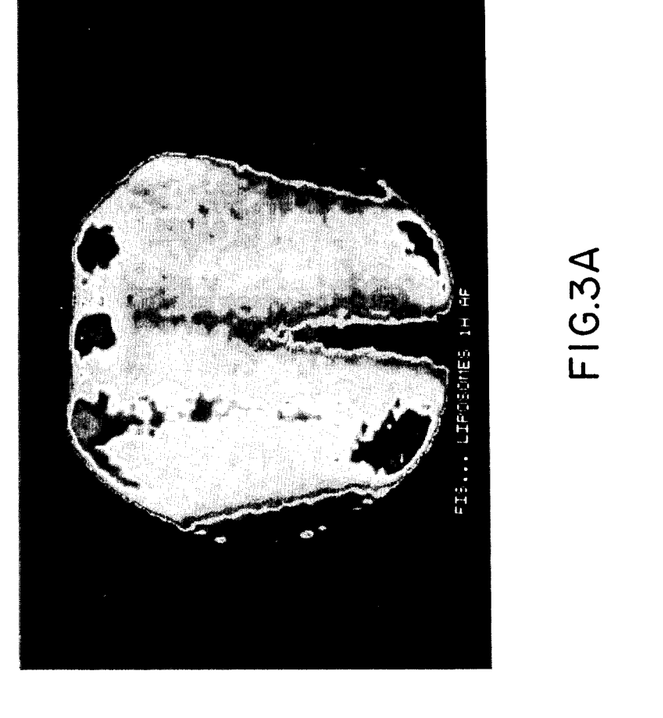

The scintigrams shown in FIGS. 3 demonstrate the tumor infiltration of the right thigh (A) and the right leg (B) in the anterior face and the right foot (C) in the posterior face in a patient who underwent ablation of a melanosarcoma of the sole of the right foot and of a metastatic ganglion of the right groin. Scintigraphy is performed 1 hour after inhalation of liposomes according to the invention. Visualization of the tumor infiltration sited between the two excised tumors is very distinct by comparison with the same zones of the healthy contralateral leg.

Patient 4

FIG. 4 corresponds to the visualization of a chain of subcutaneous metastases of a melanosarcoma of the right thigh 1 h 30 min after inhalation of the liposomes containing labelled NSPD, with quantification of the activity of the tracer in the tumor area and in the healthy contralateral zone serving as reference.

Patient 5

Visualization of pulmonary metastases of a small cell carcinoma of the base of the tongue (FIG. 5). Scintigrams obtained 1 h (in A) and 6 h (in B) after inhalation of 50 mCi of technetium according to the invention. There is an excellent correlation between the localization of the metastases obtained by scintigraphy at the sixth hour (in B) and the pulmonary radiological image.

We claim:

1. Aerosol composition for in vivo imaging or ex vivo diagnosis of tumors, which composition contains one or more soluble fragments of bacterial cell peptidoglycan of Nocardia derivatives (NSPD) which are labelled with a radioactive, paramagnetic or fluorescent element and encapsulated in liposomes and a substrate which can be used for administration by aerosol.

2. Composition as claimed in claim 1, wherein the NSPD is labelled with $^{99m}$ technetium or with another emitter detectable by scintigraphy or counting.

3. Composition as claimed in claim 1, wherein the NSPD is labelled with a paramagnetic probe.

4. Composition as claimed in claim 1, wherein the NSPD is labelled with a fluorescent probe.

5. Composition as claimed in claim 1, wherein the liposome consists of at least one lipid having substantial surfactant properties with respect to cell tissue and is thus readily emulsifiable in cell tissue.

6. Composition as claimed in claim 5, wherein the liposome is a phosphatidylcholine/phosphatidylserine/cholesterol liposome.

7. Composition as claimed in claim 6, wherein the mole ratio of the components of the liposome is 4:1:5.

8. Composition as claimed in claim 1, wherein the NSPD is in combination with one or more products possessing substantial surfactant properties with respect to cell tissue.

* * * * *